(12) United States Patent
Patel et al.

(10) Patent No.: US 10,849,896 B2
(45) Date of Patent: Dec. 1, 2020

(54) SORTILIN-BINDING SMALL MOLECULES FOR INCREASING GLUCOSE UPTAKE

(71) Applicants: University of South Florida, Tampa, FL (US); The United States Government as represented by the Department of Veterans Affairs, Washington, DC (US)

(72) Inventors: Niketa A. Patel, Land O'Lakes, FL (US); Robert Pleasants Sparks, Tampa, FL (US); Wayne Charles Guida, St. Petersburg Beach, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/022,803

(22) Filed: Jun. 29, 2018

(65) Prior Publication Data

US 2018/0318296 A1 Nov. 8, 2018

Related U.S. Application Data

(62) Division of application No. 15/151,068, filed on May 10, 2016, now abandoned.

(60) Provisional application No. 62/160,220, filed on May 12, 2015.

(51) Int. Cl.
| | |
|---|---|
| *A61K 31/498* | (2006.01) |
| *A61P 3/10* | (2006.01) |
| *A61K 31/197* | (2006.01) |
| *G16B 35/00* | (2019.01) |
| *G16C 20/60* | (2019.01) |
| *A61K 38/00* | (2006.01) |
| *A61K 31/4035* | (2006.01) |

(52) U.S. Cl.
CPC .............. *A61K 31/498* (2013.01); *A61P 3/10* (2018.01); *A61K 31/197* (2013.01); *A61K 31/4035* (2013.01); *A61K 38/00* (2013.01); *G16B 35/00* (2019.02); *G16C 20/60* (2019.02)

(58) Field of Classification Search
None
See application file for complete search history.

(56) References Cited

U.S. PATENT DOCUMENTS

| | | | | |
|---|---|---|---|---|
| 6,369,057 B1 * | 4/2002 | Billhardt | .............. | C07D 241/38 514/228.2 |
| 2007/0032474 A1 | 2/2007 | Biondi et al. | | |

* cited by examiner

*Primary Examiner* — John Pak
*Assistant Examiner* — Daniel L Branson
(74) *Attorney, Agent, or Firm* — Quarles & Brady LLP

(57) ABSTRACT

Various scaffolds of small molecules capable of binding to the active site of sortilin are identified by in silico methods. These scaffolds include norbornene anhydride amino acid adducts and 2-substituted 3-oxo-1,2,3,4-tetrahydro-2-quinoxalines. These sortilin ligands increase the uptake of glucose in 3T3L1 cells and can be employed in compositions to increase uptake of glucose for the treatment of diabetic patents.

4 Claims, 14 Drawing Sheets

SORTILIN-BINDING SMALL MOLECULES FOR INCREASING GLUCOSE UPTAKE

CROSS-REFERENCE TO RELATED APPLICATIONS

This application is a divisional of U.S. application Ser. No. 15/151,068, filed May 10, 2016, which claims the benefit of U.S. Provisional Application Ser. No. 62/160,220, filed May 12, 2015, the disclosures of which are hereby incorporated by reference in their entireties, including all figures, tables and drawings.

This invention was made with government support under VAMR 821-MR-EN-20606 awarded by Veteran Affairs. The government has certain rights in the invention.

BACKGROUND OF INVENTION

Sortilin, which is generated from sortilin WT transcript, is highly conserved across species. It has an endoplasmic reticulum (ER) import signal, a vacuolar protein sorting 10 (VSP10) luminal domain, a transmembrane domain and a cytosolic domain. Sortilin ligands bind to the VSP10 domain while the cytosolic domain contains the active sorting signal that directs sortilin and its ligands to lysosomes. Protease cleavage within the extracellular stalk of sortilin releases the sortilin ectodomain by an event called shedding. Sortilin is a major component of the Glut4 containing vesicles in adipocytes and is located in the low density microsomes along with Glut4 in the adipocytes. It plays an essential role in the development of the insulin responsive transport system in cultured adipocytes and muscle cells.

Regulation of blood glucose levels in mammals is achieved by translocation of fat and muscle specific transporter-Glut4 to the plasma membrane. Insulin resistance, inability for glucose transport by insulin, is a key hallmark of type 2 diabetes mellitus. Glut4 is often times mislocalized in diabetic patients, and more than 80% of diabetic patients are obese or overweight. It has been shown that decreasing sortilin inhibits insulin-induced glucose transport and biogenesis of insulin-responsive compartment. Morbidly obese mice have decreased sortilin which contributes to defects in glucose transport.

Discovering that sortilin levels are decreased in diabetic patients, the identification and demonstration of compounds that can stabilize sortilin and increase glucose transport in adipocytes allows the discovery of effective therapeutics for correcting defects in glucose transport and addressing obesity in diabetic patents.

DETAILED DISCLOSURE

Embodiments of the invention are directed to compounds with the ability to dock at a site within sortilin to promote the increase of glucose uptake. The compounds are identified by their ability to suitably bind to a region of the sortilin protein with high affinity and thereby mediate the interaction of sortilin with various protein molecules or other natural substrates. Compounds of three scaffolds, according to embodiments of the invention, bind to sortilin both in vivo and in silico.

Sortilin is alternatively spliced, to generate two splice variants in humans. Exon 17b, is a pseudoexon, which is absent in sortilin WT. Inclusion of this exon via alternative splicing generates a transcript with an extra coding exon between VSP10 and transmembrane domains. In neurons, downregulation of TDP-43 as seen in frontotemporal lobal degeneration, causes an increase in splice variant Sortilin 17b. It appears that splice variant sortilin 17b can bind to the sortilin ligand but is unable to efficiently mediate endocytosis. The expression of splice variants and their significance in adipocytes is not known.

The biological significance of sortilin and its role in glucose uptake is apparent by evaluating obese and lean patient samples. Primers to decipher the presence of alternatively spliced sortilin variants were designed, and experiments were carried out to analyze identified compounds for their ability to increase glucose uptake and their effect on sortilin expression on RNA and protein levels.

Figure 1:
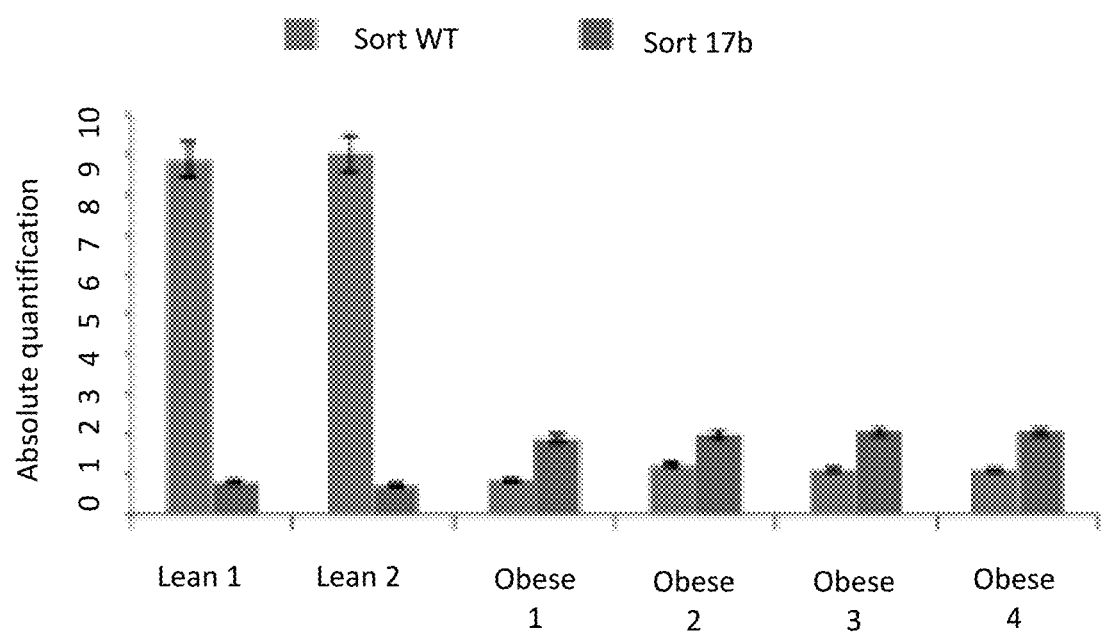
FIG. 1 shows a bar graph of the qPCR quantification of sortilin WT and 17b from non-diabetic (lean) and diabetic (obese) patients.

As obese diabetic humans have decreased sortilin expression, adipose tissue from four obese diabetic individuals and two non-diabetic individuals were obtained. RNA was isolated and real time qPCR was performed for sortilin WT and sortilin 17b. FIG. 1 shows the results of qPCR, which indicate that in lean nondiabetic individuals, sortilin WT is the predominantly expressed variant. The quantity of sortilin WT is decreased 8-fold in obese diabetic humans and the splice variant sortilin 17b is increased 2-fold.

Figure 2A:
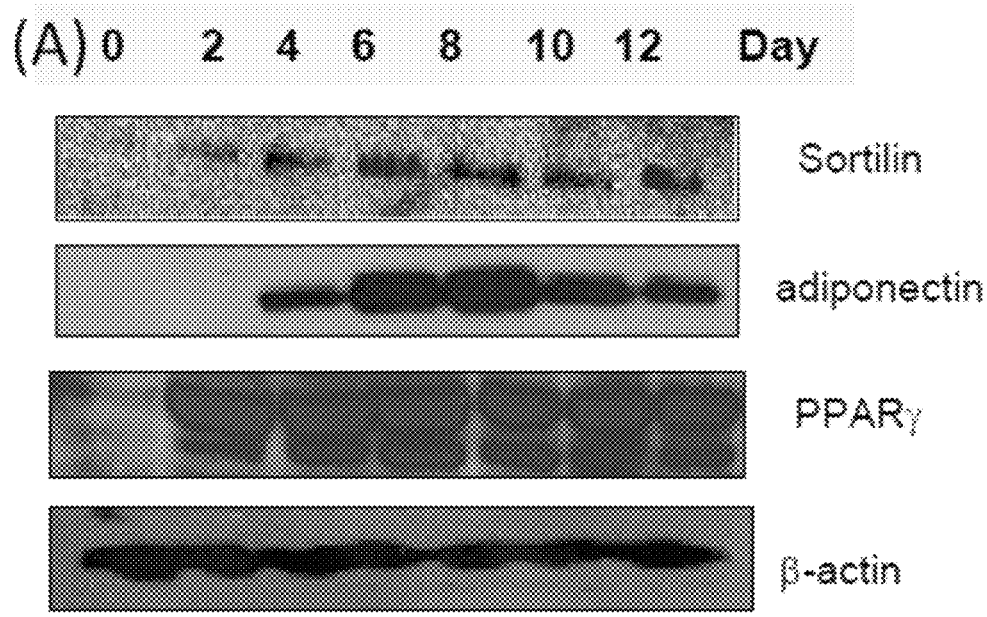
FIG. 2A shows a photograph of a silver stained Western blot analysis plate with antibodies as indicated.
Figure 2B:
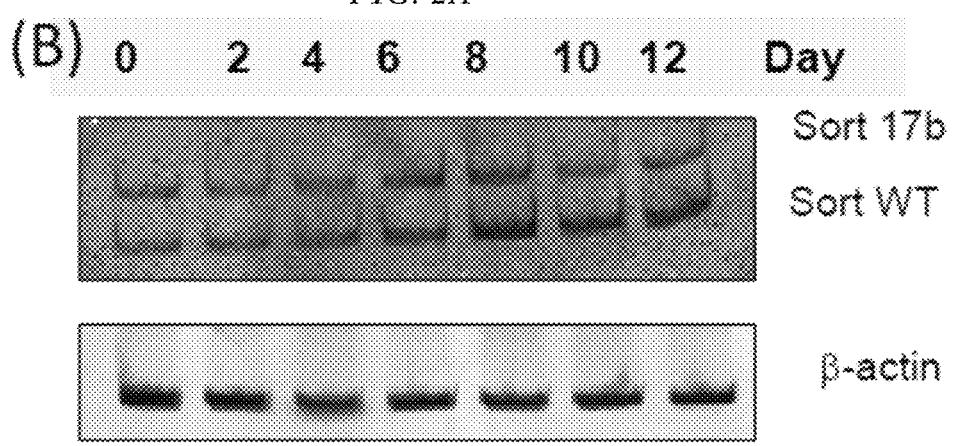
FIG. 2B shows a photograph of a silver stained PCR plate for sortilin WT and 17b.
Figure 3:
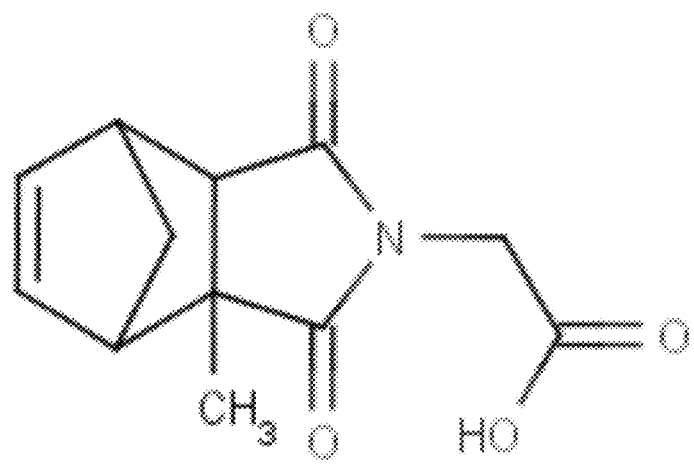
FIG. 3 shows the structure of the scaffold 1 exemplary compound, 2-methyl-3,5-dioxo-4-azatricyclo[5.2.1.0(2,6)]dec-8-en-4-yl)acetic acid, and a Schrödinger Glide graphical representation of its binding to sortilin, according to an embodiment of the invention.
Figure 3:
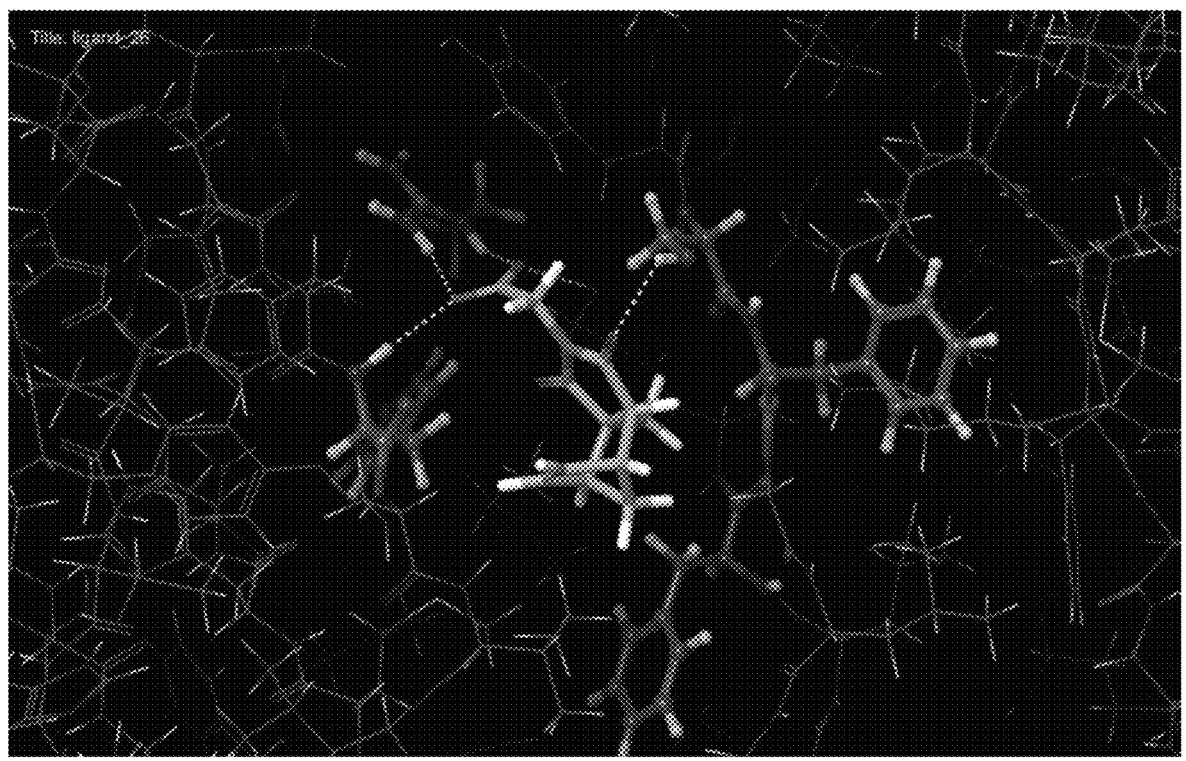
Figure 4:
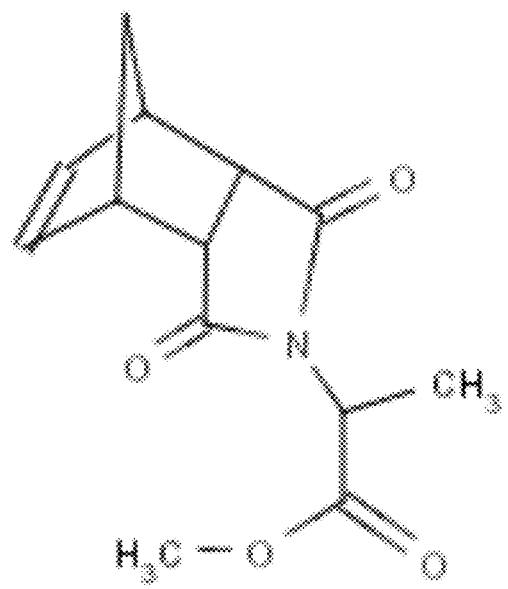
FIG. 4 shows the structure of the scaffold 1 exemplary compound, methyl 2-(1,3-dioxo-1,3,3a,4,7,7a-hexahydro-2H-4,7-methanoisoindol-2-yl)propanoate, and a Schrödinger Glide graphical representation of its binding to sortilin, according to an embodiment of the invention.
Figure 4:
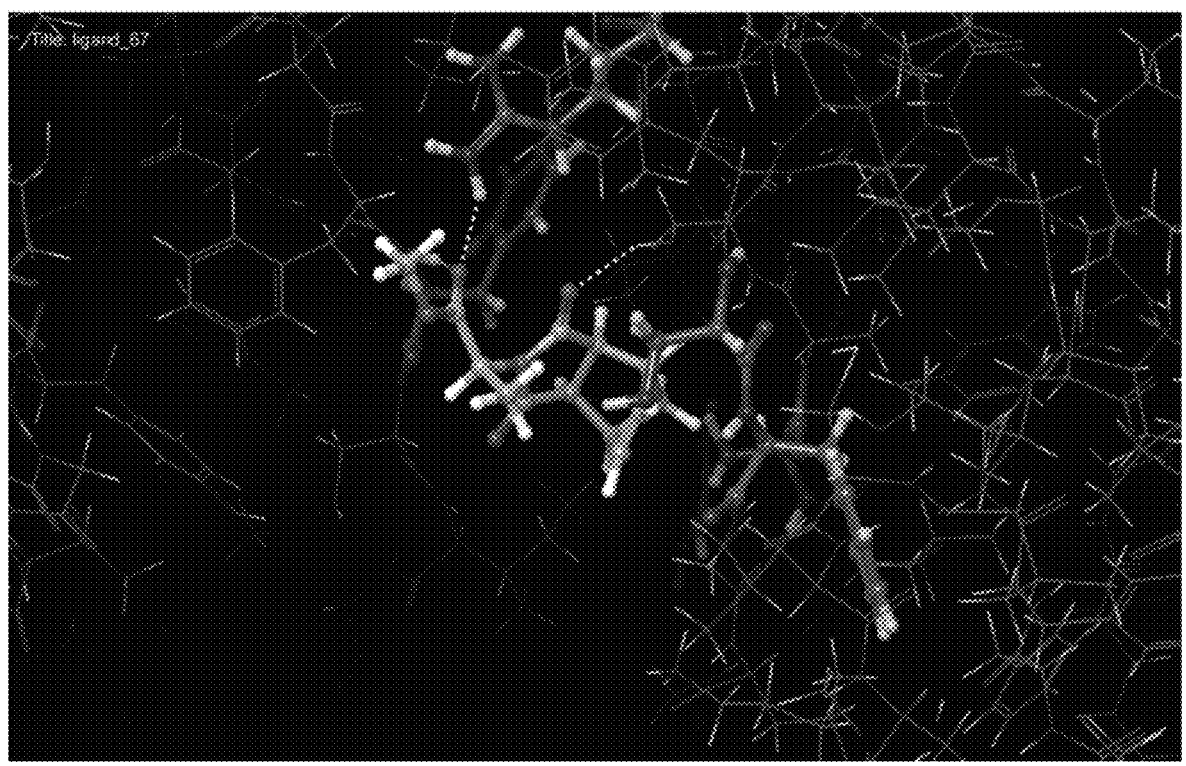
Figure 5:
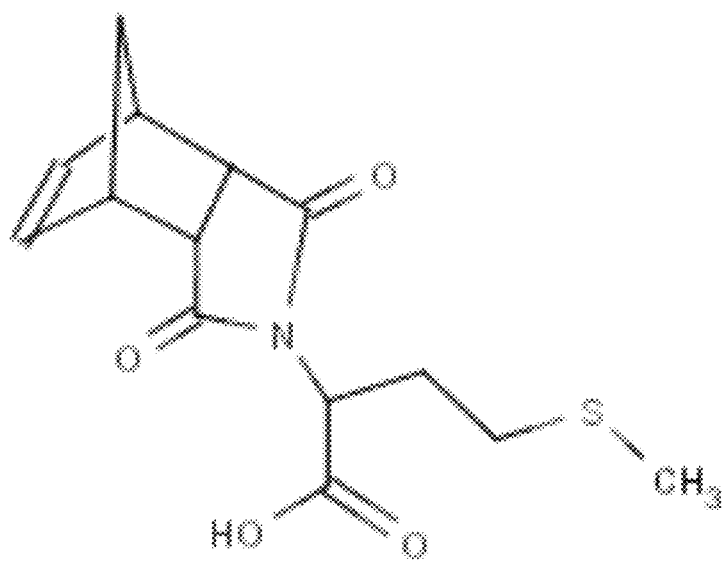
FIG. 5 shows the structure of the scaffold 1 exemplary compound, 2-(1,3-dioxo-1,3,3a,4,7,7a-hexahydro-2H-4,7-methanoisoindol-2-yl)-4-(methylthio)butanoic acid, and a Schrödinger Glide graphical representation of its binding to sortilin, according to an embodiment of the invention.
Figure 5:
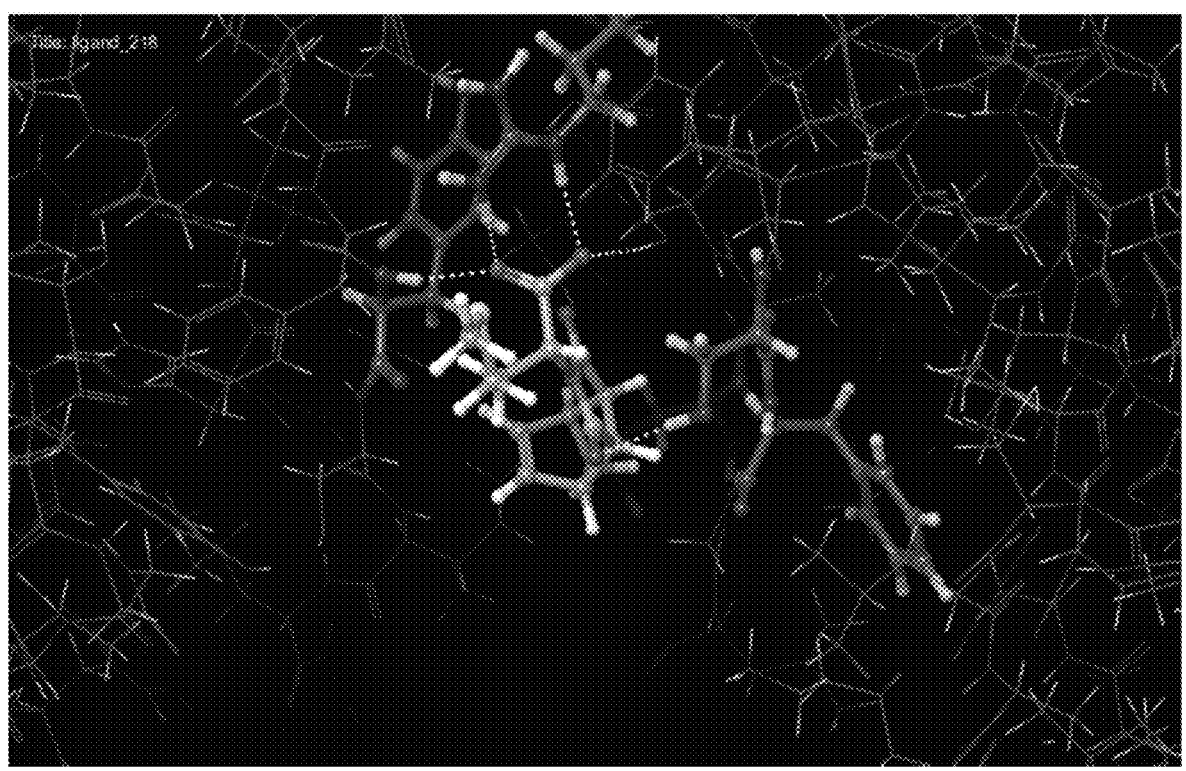
Figure 6:
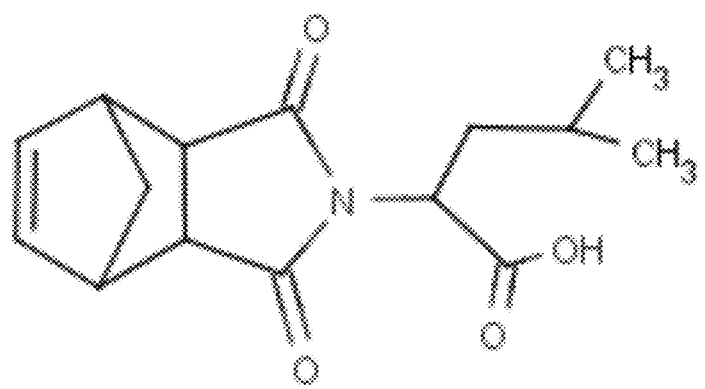
FIG. 6 shows the structure of the scaffold 1 exemplary compound, 2-(3,5-dioxo-4-azatricyclo[5.2.1.0(2,6)]dec-8-en-4-yl)-4-methylpentanoic acid, and a Schrödinger Glide graphical representation of its binding to sortilin, according to an embodiment of the invention.
Figure 6:
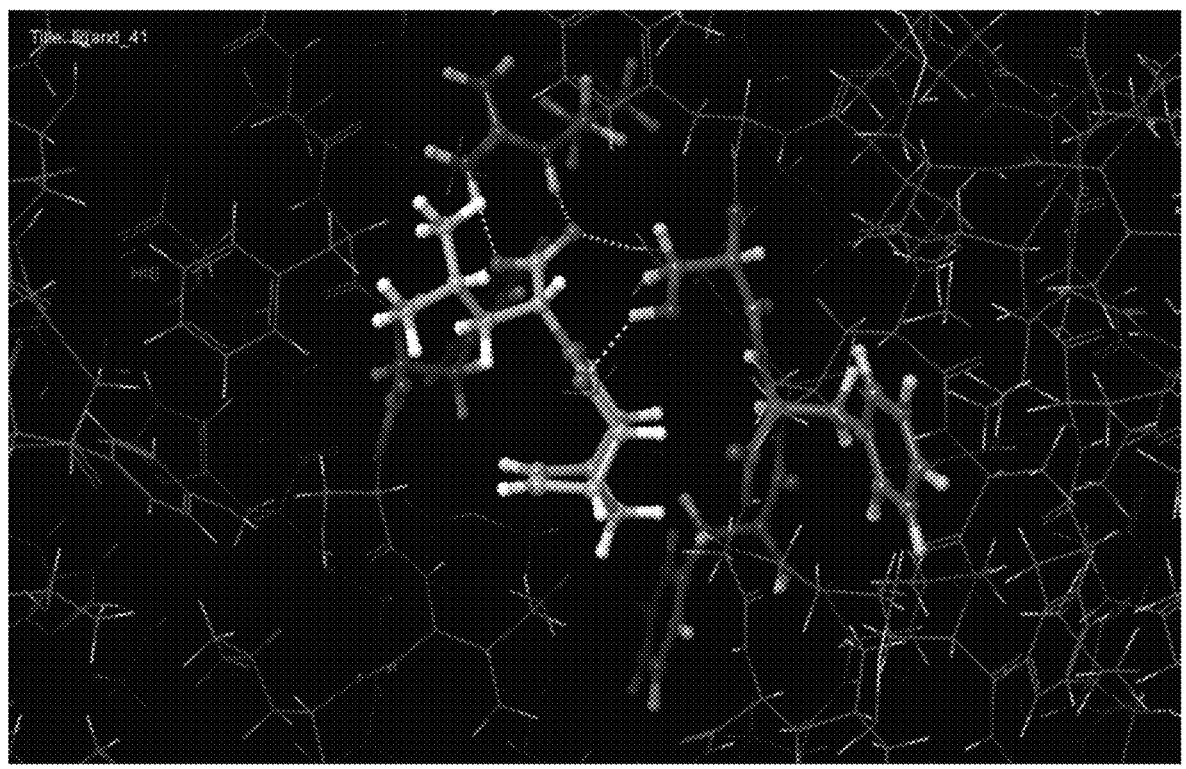
Figure 7:
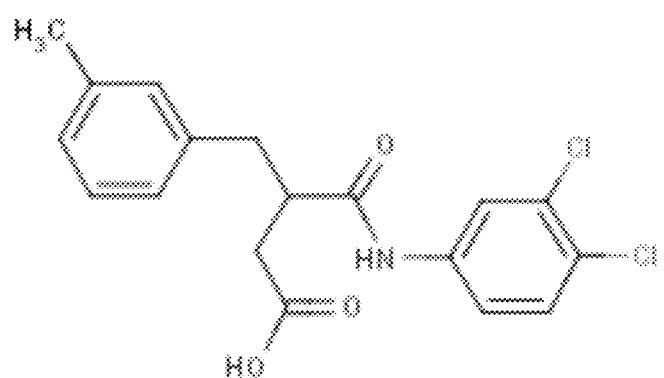
FIG. 7 shows the structure of the scaffold 2 exemplary compound, 4-[(3,4-dichlorophenyl)amino]-3-(3-methylbenzyl)-4-oxobutanoic acid, and a Schrödinger Glide graphical representation of its binding to sortilin, according to an embodiment of the invention.
Figure 7:
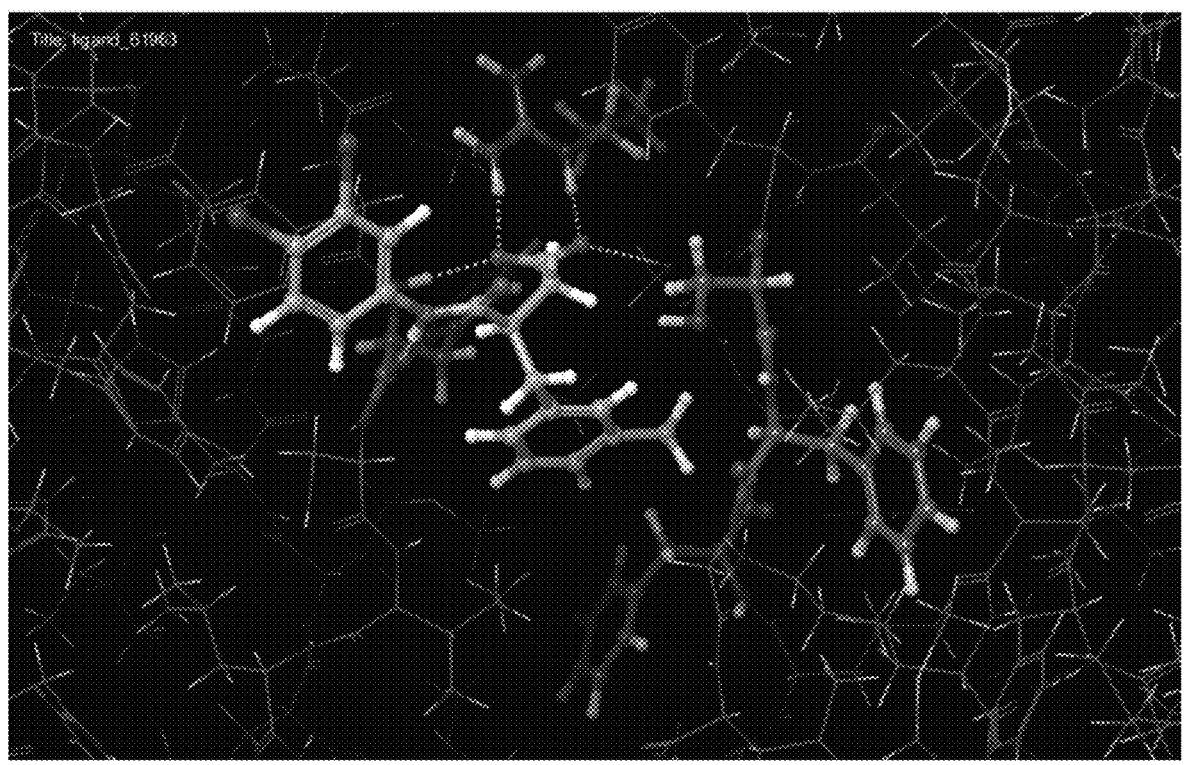
Figure 8:
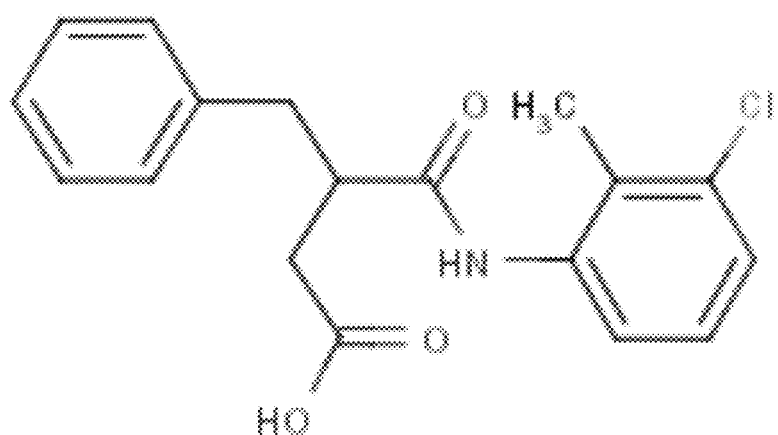
FIG. 8 shows the structure of the scaffold 2 exemplary compound, 3-benzyl-4-[(3-chloro-2-methylphenyl)amino]-4-oxobutanoic acid, and a Schrödinger Glide graphical representation of its binding to sortilin, according to an embodiment of the invention.
Figure 8:
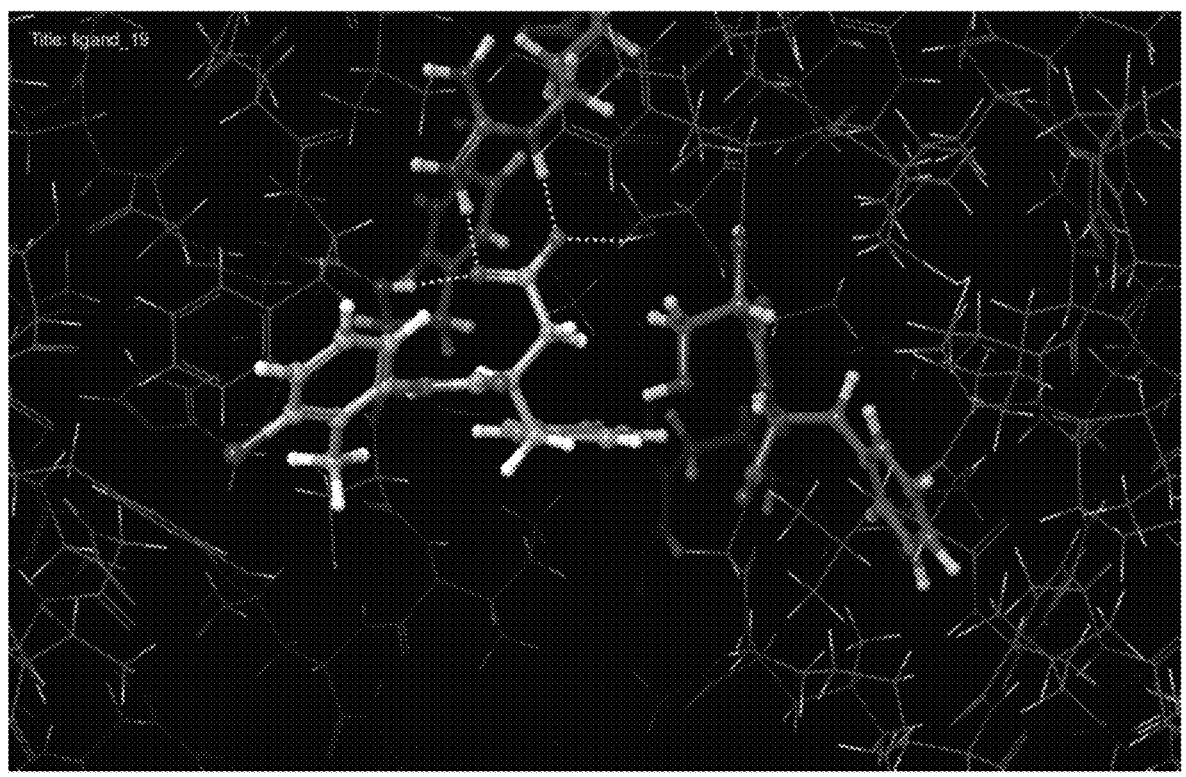
Figure 9:
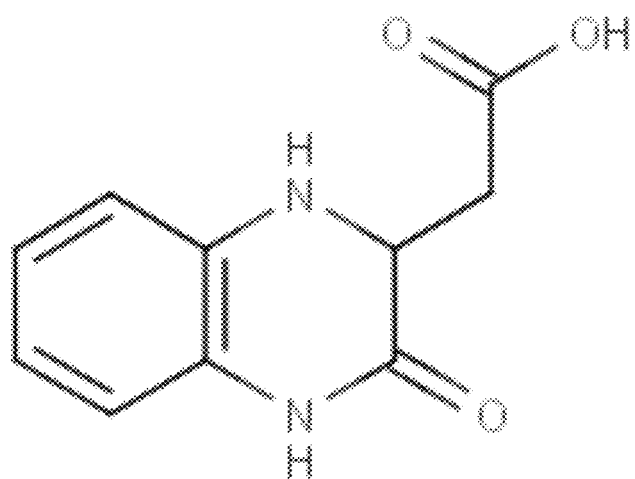
FIG. 9 shows the structure of the scaffold 3 exemplary compound, (3-oxo-1,2,3,4-tetrahydro-2-quinoxalinyl)acetic acid, and a Schrödinger Glide graphical representation of its binding to sortilin, according to an embodiment of the invention.
Figure 9:
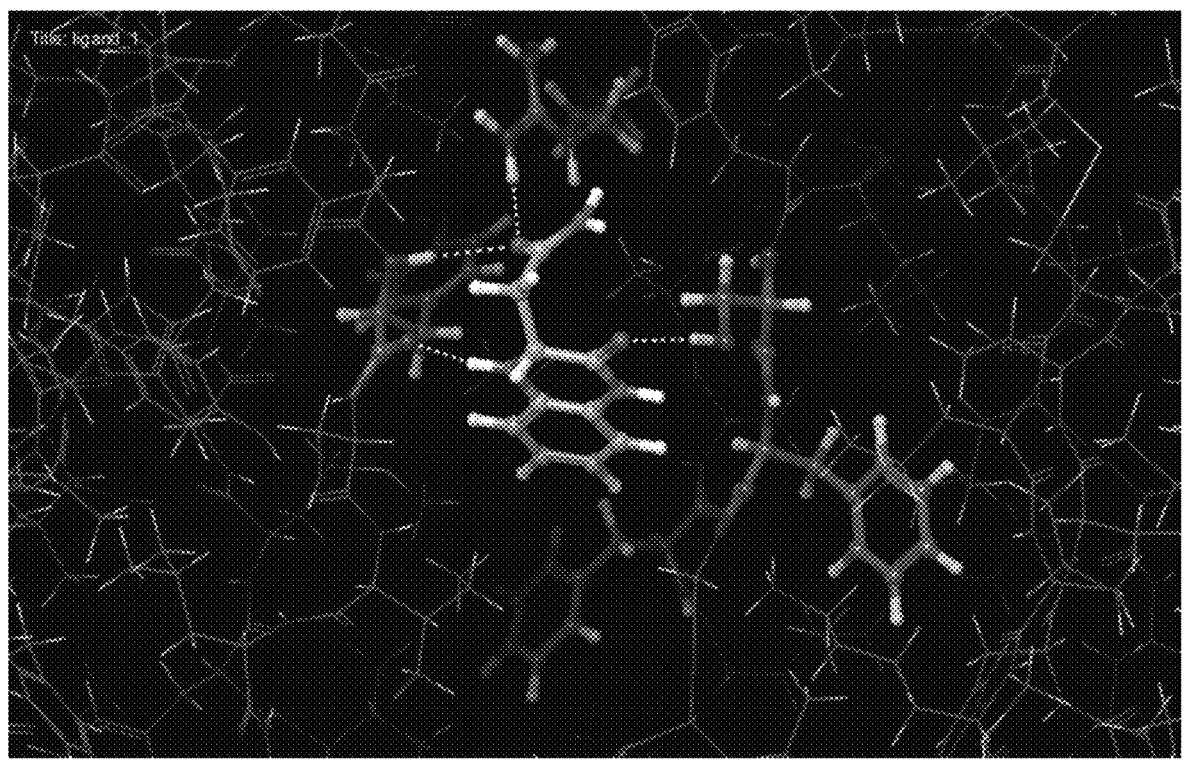

Expression of sortilin in mouse 3T3L1 adipocytes serves as an in vitro model for studying human adipogenesis and mechanisms underlying obesity, as further human and mouse sortilin have >90% homology. The 3T3L1 murine preadipocyte cell line is widely used, as it authentically reproduces adipogenesis including expression of adipogenic genes and morphological changes. Studies of the expression of sortilin splice variants during adipogenesis indicate that both variants (WT and 17b) are expressed during adipogenesis. The level of sortilin WT increases as adipocytes mature, from day 6 onward, while sortilin 17b levels decline in mature adipocytes. FIG. 2A shows western blot analysis, where sortilin antibody does not distinguish between variants; PPARγ and adiponectin are markers of adipogenesis. FIG. 2B shows PCR using primers that simultaneously amplify sortilin WT and sortilin 17b. Clearly sortilin WT increases by day 6 while sortilin 17b decreases upon adipocyte maturation.

A docking scheme was constructed and used to conduct virtual screens of sortilin for small molecules that bind to sortilin in a correct orientation. Identification of small molecules suitable for testing as potential ligands for sortilin, in silico screening of potential compounds was carried out using Schrödinger software. The screening proceeded by constructing a suitable structure of sortilin from the protein data bank with structure 3F6K using the Schrödinger Protein Prep Wizard. Ligands were assembled from the NCI Diversity set IV and from Chembridge's commercially procurable databases. Potential ligands and, subsequently, suitable analogues were found via the Chembridge compound libraries. The virtual ligands were procured and prepared using Schrödinger Ligprep. Resulting compounds are scrutinized and suitable compounds are selected for testing. Software is employed to generate analogues of these ligands and prepared virtual structures for docking. Target ligands are subsequently procured from commercial sources, when possible, and tested for various activities in adipocytes, including adipocyte differentiation and glucose uptake effects by the presence of these molecules.

Specifically, virtual compounds were docked into the active site and scoring was biased to electrostatic interactions, particularly hydrogen bonding, with sortilin at amino acid residues: Serine 272, Arginine 292, Phenylalanine 273, Serine 283 and Tyrosine 318. Docking was performed using Schrödinger Glide on settings HTVS, SP, and XP. Further docking was refined using the Schrödinger Quantum Polarized Ligand Docking (QPLD). After this enrichment and refinement of results for selection of ligands, compounds were tested in vivo. Preliminary targets were selected from the Chembridge library or other databases of compounds, based on various ADME properties and in regard to an overall docking score from the various virtual screenings performed.

Small molecule compounds for the stimulation of increased glucose uptake, according to embodiments of the invention, are of three identified molecular scaffolds. The three molecular scaffolds were identified for testing due to suitable log p to permeate the cell membrane and reach sortilin within the cell. Species of the first scaffold are norbornene anhydride amino acid adducts (including the monocarbonyl reduced equivalent norbornene amide carboxylates) and esters thereof, as shown below, and represented by the compounds: 2-methyl-3,5-dioxo-4-azatricyclo [5.2.1.0(2,6)]dec-8-en-4-yl)acetic acid; methyl 2-(1,3-dioxo-1,3,3a,4,7,7a-hexahydro-2H-4,7-methanoisoindol-2-yl)propanoate; 2-(1,3-dioxo-1,3,3a,4,7,7a-hexahydro-2H-4,7-methanoisoindol-2-yl)-4-(methylthio)butanoic acid; and 2-(3,5-dioxo-4-azatricyclo[5.2.1.0(2,6)]dec-8-en-4-yl)-4-methylpentanoic acid.

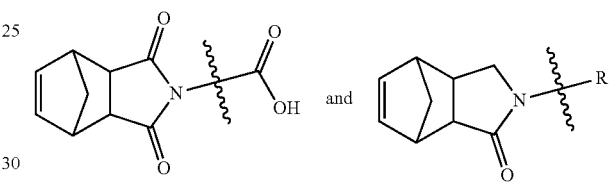

where R is a carboxylic acid or ester thereof and where any of the carbons of the norbornene ring can be substituted with a $C_1$ to C6 alkyl group or the carboxylic acid can be condensed as a $C_1$ to $C_5$ ester.

The second scaffolds are N-phenyl-amide-acids of benzyl substituted glutaric acid as shown below, and represented by the two compounds: 4-[(3,4-dichlorophenyl)amino]-3-(3-methylbenzyl)-4-oxobutanoic acid; and 3-benzyl-4-[(3-chloro-2-methylphenyl)amino]-4-oxobutanoic acid.

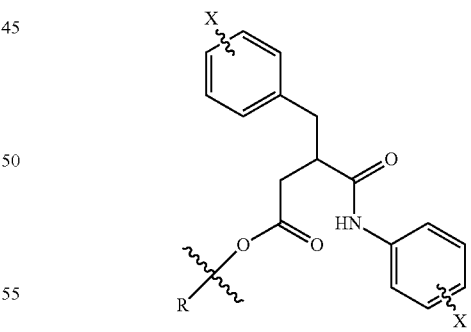

where X is independently $C_1$ to $C_5$ alkyl, acyl, amino, sulfono, chloro, bromo, iodo, or flouro and R can be $C_1$ to $C_5$ alkyl, or the acid can be replaced with a tetrazol. The methylene units can independently be lengthened to ethylene or propylene units.

The third scaffold is 2 substituted 3-oxo-1,2,3,4-tetrahydro-2-quinoxalines, shown below and represented by the compound (3-oxo-1,2,3,4-tetrahydro-2-quinoxalinyl)acetic acid.

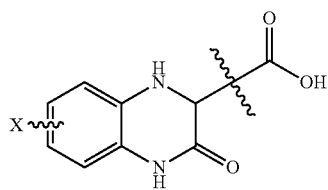

where x is $C_1$ to $C_5$ alkyl, acyl, amino, sulfono, chloro, bromo, iodo, or flouro and where the carboxylic acid may be separated from the ring by one to three carbons which may be substituted with a $C_1$ to $C_5$ alkyl. The acid may be converted to a $C_1$ to $C_5$ ester, or replaced with a tetrazole.

The structures of potential ligands from the three scaffolds and the graphical binding to the active site of a sortilin are shown in FIGS. 3-9. Other species of the three scaffolds, according to embodiments of the invention, are given in Table 1, below, where the title can be matched with the chemical structure of FIG. 10.

TABLE 1

Figure 10:
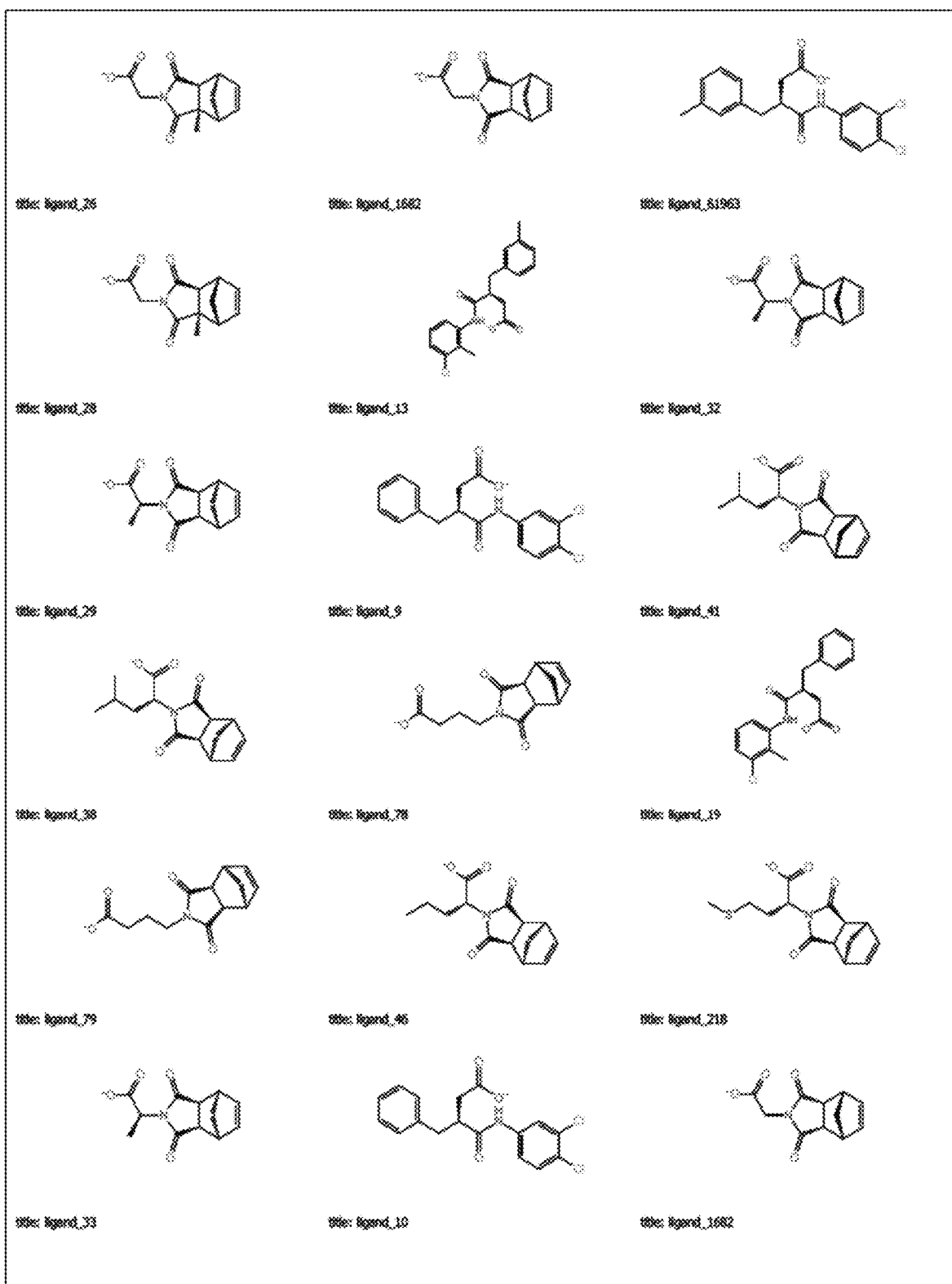
FIG. 10 shows various species of Scaffolds 1-3, according to embodiments of the invention.
Figure 10:
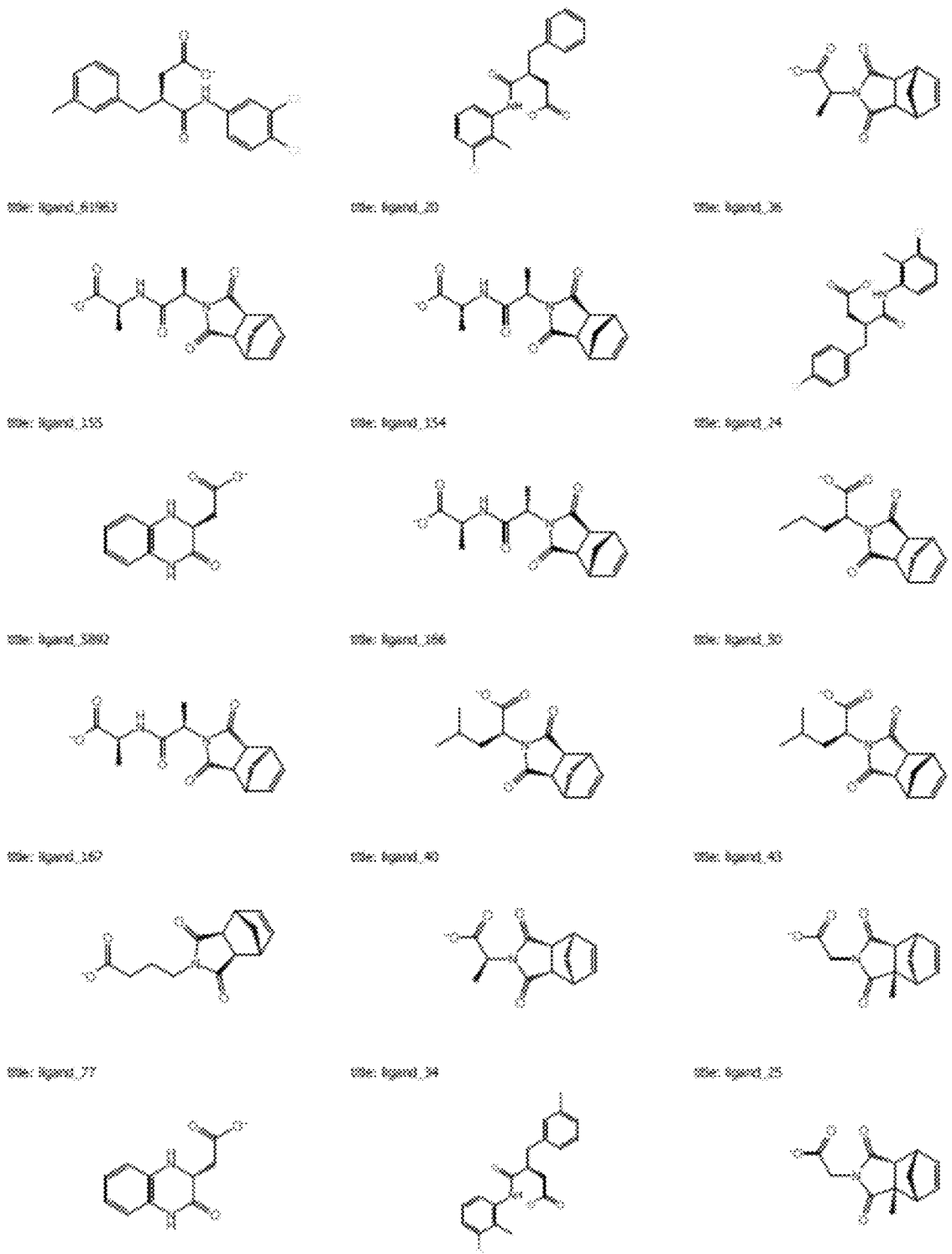
Figure 10:
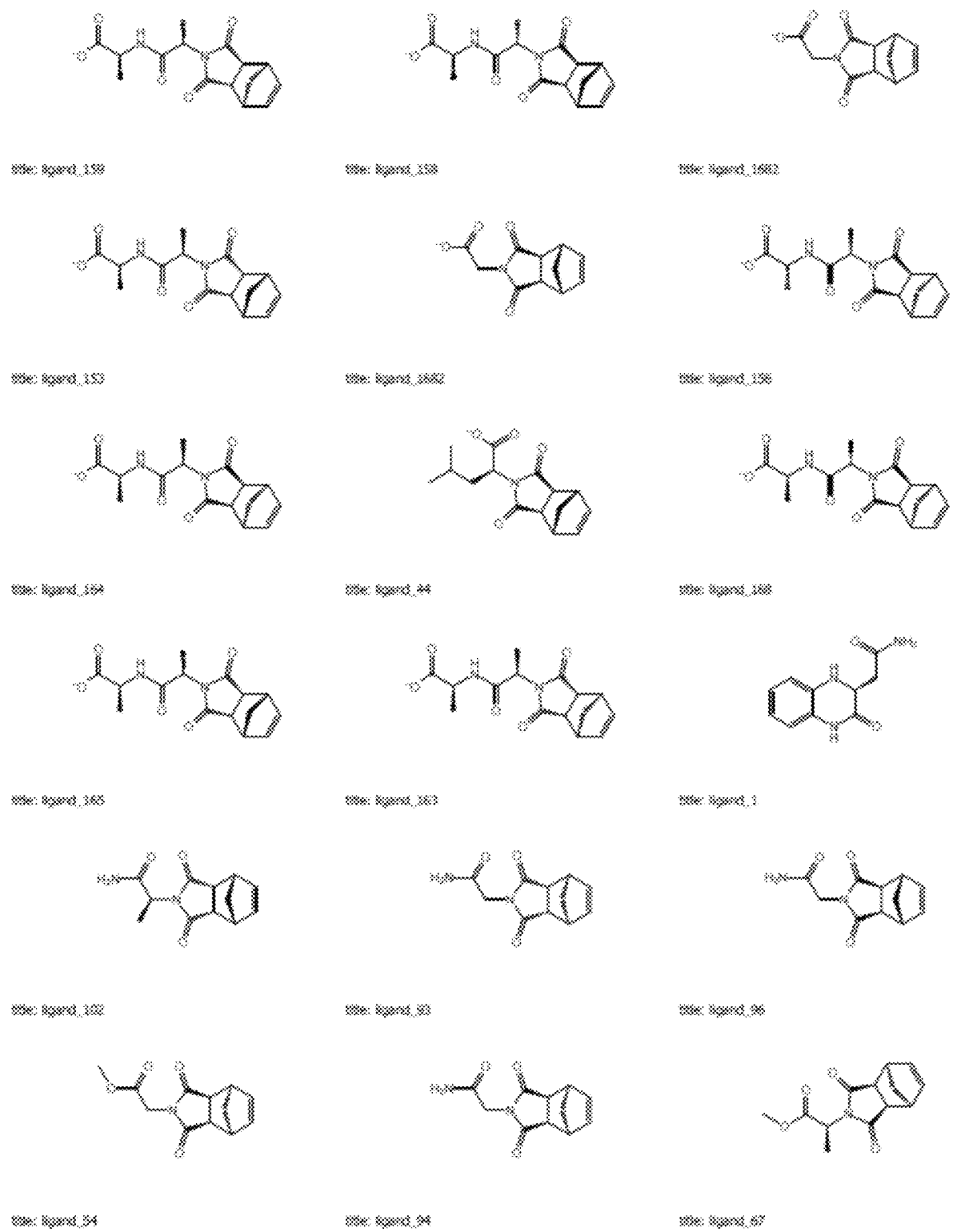

Species of the Three Scaffolds, where structures are given in FIG. 10

| Title | Entry ID | RMS Derivative-OPLS-2005 | Glide lignum | Docking score | Glide gscore | Glide lipo | Glide hbond |
|---|---|---|---|---|---|---|---|
| ligand_26 | 1928 | 0.039 | 26 | −9.994 | −9.994 | −2.382 | −0.72 |
| ligand_1682 | 1929 | 0.034 | 296 | −9.803 | −9.803 | −2.044 | −0.729 |
| ligand_61963 | 1930 | 0.028 | 299 | −9.781 | −9.781 | −2.832 | −1.04 |
| ligand_28 | 1931 | 0.019 | 28 | −9.71 | −9.71 | −2.027 | −0.86 |
| ligand_13 | 1932 | 0.006 | 13 | −9.586 | −9.586 | −2.785 | −1.025 |
| ligand_32 | 1933 | 0.023 | 32 | −9.573 | −9.573 | −2.026 | −0.742 |
| ligand_29 | 1934 | 0.002 | 29 | −9.569 | −9.569 | −2.019 | −0.743 |
| ligand_9 | 1935 | 0.015 | 9 | −9.516 | −9.516 | −2.552 | −1.034 |
| ligand_41 | 1936 | 0.007 | 41 | −9.46 | −9.46 | −2.083 | −0.707 |
| ligand_38 | 1937 | 0 | 38 | −9.352 | −9.352 | −2.093 | −0.78 |
| ligand_78 | 1938 | 0.038 | 78 | −9.329 | −9.329 | −2.008 | −0.982 |
| ligand_19 | 1939 | 0.002 | 19 | −9.32 | −9.32 | −2.431 | −1.025 |
| ligand_79 | 1940 | 0.001 | 79 | −9.307 | −9.307 | −1.991 | −1.009 |
| ligand_46 | 1941 | 0.005 | 46 | −9.275 | −9.275 | −2.031 | −0.755 |
| ligand_218 | 1942 | 0.005 | 218 | −9.166 | −9.166 | −2.023 | −0.717 |
| ligand_33 | 1943 | 0.023 | 33 | −9.134 | −9.134 | −1.918 | −0.745 |
| ligand_10 | 1944 | 0.049 | 10 | −9.002 | −9.002 | −2.485 | −0.954 |
| ligand_1682 | 1945 | 0.012 | 293 | −8.916 | −8.916 | −1.698 | −0.753 |
| ligand_61963 | 1946 | 0.047 | 300 | −8.877 | −8.877 | −2.738 | −0.709 |
| ligand_20 | 1947 | 0.038 | 20 | −8.81 | −8.81 | −2.552 | −0.94 |
| ligand_36 | 1948 | 0.001 | 36 | −8.678 | −8.678 | −1.719 | −0.755 |
| ligand_155 | 1949 | 0.003 | 155 | −8.49 | −8.49 | −0.721 | −1.082 |
| ligand_154 | 1950 | 0.013 | 154 | −8.484 | −8.484 | −0.719 | −1.086 |
| ligand_24 | 1951 | 0.049 | 24 | −8.477 | −8.477 | −2.646 | −0.823 |
| ligand_5892 | 1952 | 0.014 | 298 | −8.447 | −8.447 | −0.739 | −0.999 |
| ligand_166 | 1953 | 0.023 | 166 | −8.44 | −8.44 | −1.055 | −0.733 |
| ligand_50 | 1954 | 0.029 | 50 | −8.434 | −8.434 | −1.742 | −0.754 |
| ligand_167 | 1955 | 0.01 | 167 | −8.42 | −8.42 | −1.055 | −0.731 |
| ligand_40 | 1956 | 0.017 | 40 | −8.408 | −8.408 | −1.76 | −0.751 |
| ligand_43 | 1957 | 0.008 | 43 | −8.405 | −8.405 | −1.758 | −0.751 |
| ligand_77 | 1958 | 0.001 | 77 | −8.38 | −8.38 | −1.054 | −0.752 |
| ligand_34 | 1959 | 0.026 | 34 | −8.35 | −8.35 | −1.399 | −0.72 |
| ligand_25 | 1960 | 0.006 | 25 | −8.314 | −8.314 | −1.371 | −0.728 |
| ligand_5892 | 1961 | 0.016 | 297 | −8.241 | −8.241 | −1.665 | −1.15 |
| ligand_14 | 1962 | 0.018 | 14 | −8.207 | −8.207 | −2.31 | −0.671 |
| ligand_27 | 1963 | 0.007 | 27 | −8.201 | −8.201 | −1.237 | −0.731 |
| ligand_159 | 1964 | 0.026 | 159 | −8.159 | −8.159 | −0.795 | −0.728 |
| ligand_158 | 1965 | 0.018 | 158 | −8.155 | −8.155 | −0.801 | −0.727 |
| ligand_1682 | 1966 | 0.047 | 295 | −8.146 | −8.146 | −1.019 | −0.733 |
| ligand_153 | 1967 | 0.024 | 153 | −8.135 | −8.135 | −0.885 | −0.728 |
| ligand_1682 | 1968 | 0.037 | 294 | −8.133 | −8.133 | −1.026 | −0.743 |
| ligand_156 | 1969 | 0.012 | 156 | −8.097 | −8.097 | −0.649 | −1.015 |
| ligand_164 | 1970 | 0.018 | 164 | −8.057 | −8.057 | −0.777 | −0.871 |
| ligand_44 | 1971 | 0.003 | 44 | −8.027 | −8.027 | −1.561 | −0.689 |
| ligand_168 | 1972 | 0.033 | 168 | −8.024 | −8.024 | −0.79 | −0.72 |
| ligand_165 | 1973 | 0.045 | 165 | −8.019 | −8.019 | −0.847 | −0.722 |
| ligand_163 | 1974 | 0.024 | 163 | −8.002 | −8.002 | −0.779 | −0.866 |
| ligand_1 | 1975 | 0.001 | 1 | −7.289 | −7.289 | −1.72 | −0.868 |
| ligand_102 | 1976 | 0.015 | 102 | −7.222 | −7.222 | −2.047 | −0.574 |
| ligand_93 | 1977 | 0.039 | 93 | −7.187 | −7.187 | −2.063 | −0.604 |
| ligand_96 | 1978 | 0.029 | 96 | −7.186 | −7.186 | −2.063 | −0.607 |
| ligand_54 | 1979 | 0.023 | 54 | −7.151 | −7.151 | −2.091 | −0.725 |
| ligand_94 | 1980 | 0.017 | 94 | −7.128 | −7.128 | −1.936 | −0.664 |
| ligand_67 | 1981 | 0.017 | 67 | −7.093 | −7.093 | −2.093 | −0.728 |
| ligand_104 | 1982 | 0.002 | 104 | −7.07 | −7.07 | −2.085 | −0.603 |
| ligand_66 | 1983 | 0.035 | 66 | −7.063 | −7.063 | −2.088 | −0.723 |
| ligand_101 | 1984 | 0.003 | 101 | −7.054 | −7.054 | −2.083 | −0.603 |
| ligand_111 | 1985 | 0.003 | 111 | −7.053 | −7.053 | −2.112 | −0.6 |
| ligand_112 | 1986 | 0.005 | 112 | −7.047 | −7.047 | −2.129 | −0.604 |

TABLE 1-continued

Species of the Three Scaffolds, where structures are given in FIG. 10

| Title | Entry ID | RMS Derivative-OPLS-2005 | Glide lignum | Docking score | Glide gscore | Glide lipo | Glide hbond |
|---|---|---|---|---|---|---|---|
| ligand_141 | 1987 | 0.013 | 141 | −7.041 | −7.041 | −1.963 | −0.696 |
| ligand_144 | 1988 | 0.028 | 144 | −7.034 | −7.034 | −1.963 | −0.694 |
| ligand_110 | 1989 | 0.017 | 110 | −7.033 | −7.033 | −2.103 | −0.603 |
| ligand_99 | 1990 | 0.047 | 99 | −7.014 | −7.014 | −2.118 | −0.591 |

In embodiments of the invention, pharmaceutical compositions and dosage formulations involve one or more of these species from any of the three scaffolds combined with other vehicles for administration, such as, solvents, buffering agents, transporters, salts, binders, fillers, disintegrants, lubricants, encapsulates, emulsifiers, suspending agents, penetration enhancers, flavoring agents, preservatives, coloring agents, propellants, and/or one or more additional therapeutic agents. These components are combined with the sortilin ligand, for a desired mode of delivery, or for an improvement of therapeutic effectiveness of these ligands, by improving absorption, distribution, metabolism, and excretion (ADME) characteristics and/or improving the timing of therapeutics, such as time release modifications. The composition can be administered intravenously, orally, rectally, sublingually, sublabially, epidurally, intracerebrally, intracerebroventrically, topically, nasally, intervitrally, subcutaneously, transdermally, by inhalation, or in any other manner of administration.

Examples of dosage forms include, but are not limited to: tablets; caplets; capsules; cachets; troches; lozenges; dispersions; suppositories; ointments; cataplasms; pastes; powders; dressings; creams; plasters; solutions; patches; aerosols; gels; aqueous or non-aqueous liquid suspensions; oil-in-water or water-in-oil liquid emulsions; solutions; and elixirs. Solvents for liquid solutions or suspensions include, but are not limited to, one or more of water, glycols, oils, ethanol or other alcohols. Excipients for solid forms include, but are not limited to, one or more of starches, sugars, and micro-crystalline cellulose. Pharmaceutically acceptable additives include: suspending agents, such as, but not limited to, one or more of sorbitol syrup, cellulose derivatives and hydrogenated edible fats. Emulsifying agents, such as, but not limited to, one or more of lecithin, acacia, almond oil, oily esters, ethyl alcohol, fractionated vegetable oils. Preservatives include, but not limited to, one or more of methyl-p-hydroxybenzoate, propyl-p-hydroxybenzoate, and sorbic acid. Binders include, but are not limited to, one or more of corn starch, potato starch, or other starches, gelatin, acacia, sodium alginate, alginic acid, powdered tragacanth, guar gum, cellulose, ethyl cellulose, cellulose acetate, carboxymethyl cellulose calcium, sodium carboxymethyl cellulose, polyvinyl pyrrolidone, methyl cellulose, pre-gelatinized starch, hydroxypropyl methyl cellulose, and microcrystalline cellulose. Fillers include, but are not limited to, one or more of talc, calcium carbonate, microcrystalline cellulose, powdered cellulose, dextrates, kaolin, mannitol, silicic acid, sorbitol, starch, and pre-gelatinized starch. Disintegrants include, but are not limited to, one or more of agar-agar, alginic acid, calcium carbonate, microcrystalline cellulose, croscarmellose sodium, crospovidone, polacrilin potassium, sodium starch glycolate, potato starch, tapioca starch, pre-gelatinized starch, and clays. Lubricants include, but are not limited to, one or more calcium stearate, magnesium stearate, mineral oil, light mineral oil, glycerin, sorbitol, mannitol, polyethylene glycol, stearic acid, sodium lauryl sulfate, talc, hydrogenated peanut oil, hydrogenated cottonseed oil, hydrogenated sunflower oil, hydrogenated sesame oil, olive oil, hydrogenated corn oil, hydrogenated soybean oil, zinc stearate, ethyl oleate, ethyl laureate, agar, syloid silica gel, coagulated aerosol of synthetic silica, and pyrogenic silicon dioxide. Penetration enhancers include, but are not limited to, one or more of acetone, ethanol, dimethyl sulfoxide, dimethyl acetamide, dimethyl formamide, polyethylene glycol, polyvinylpyrrolidone, urea, Tween 80, and Span 60. The pH of pharmaceutical compositions, dosage forms, or the tissue to which the pharmaceutical composition or dosage form is applied, can be adjusted to improve delivery of one or more active ingredients. Propellants include, but are not limited to, dichlorodifluoromethane, trichlorofluoromethane, dichlorotetrafluoroethane, tetrafluoroethane, hexafluoropropane, and carbon dioxide.

Figures 11A, 11B:
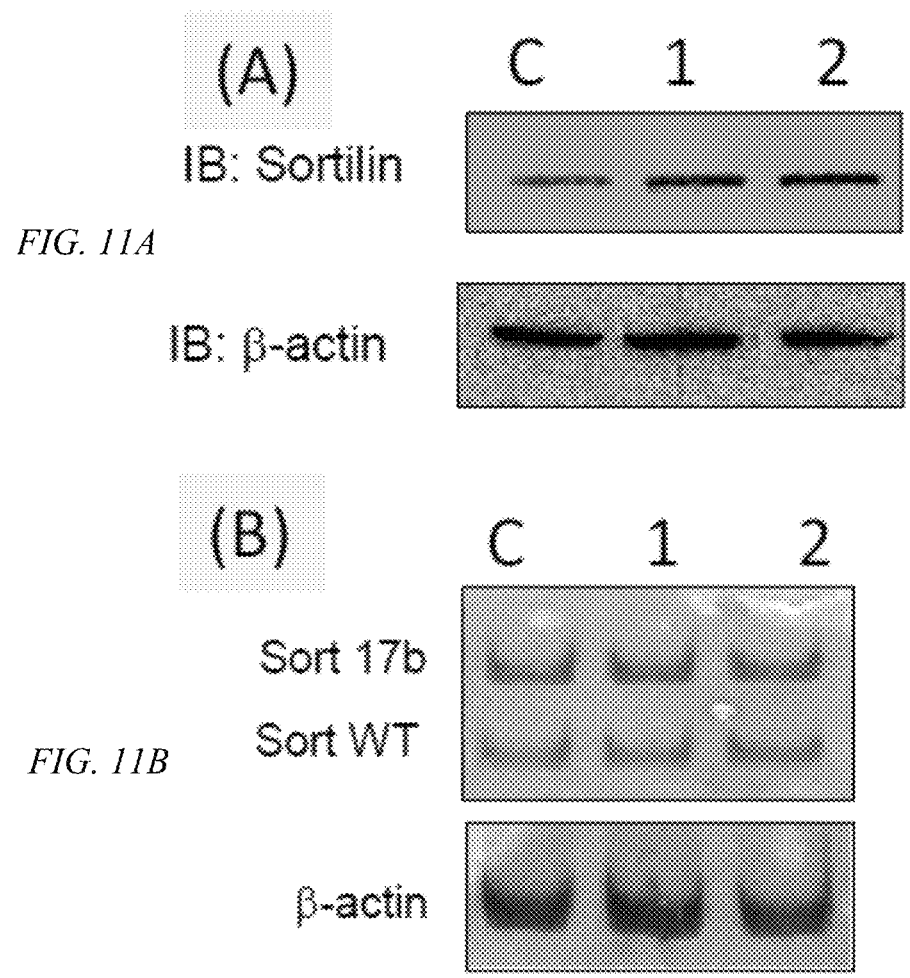
FIG. 11 shows photographs of FIG. 11A silver stained plates for Western blot analysis with antibodies and FIG. 11B silver stained plates for PCR for sortilin WT and 17b where C is Control, 1 is 2-(3,5-dioxo-4-azatricyclo[5.2.1.0(2,6)]dec-8-en-4-yl)-4-methylpentanoic acid, and 2 is 4-[(3,4-dichlorophenyl)amino]-3-(3-methylbenzyl)-4-oxobutanoic acid.

Methods and Materials 2-(3,5-Dioxo-4-azatricyclo[5.2.1.0~2,6~]dec-8-en-4-yl)-4-methylpentanoic acid and 4-[(3,4-dichlorophenyl)amino]-3-(3-methylbenzyl)-4-oxobutanoic acid were used to treat 3T3L1 cells at 500 nM concentration on day 3 of differentiation and maintained in culture up to day 8 when the cells mature into adipocytes with well-developed lipid bodies. Whole cell lysate was isolated and western blot analysis was performed using anti-sortilin antibody. Results are given in FIG. 11A, which indicate increase in sortilin expression in the presence of these compounds. To determine the compounds effect sortilin gene expression, 3T3L1 cells were treated as above and total RNA was isolated. RT-PCR was performed using sortilin primers. FIG. 11A shows that the mRNA levels of sortilin were not affected by the compounds.

Figure 12:
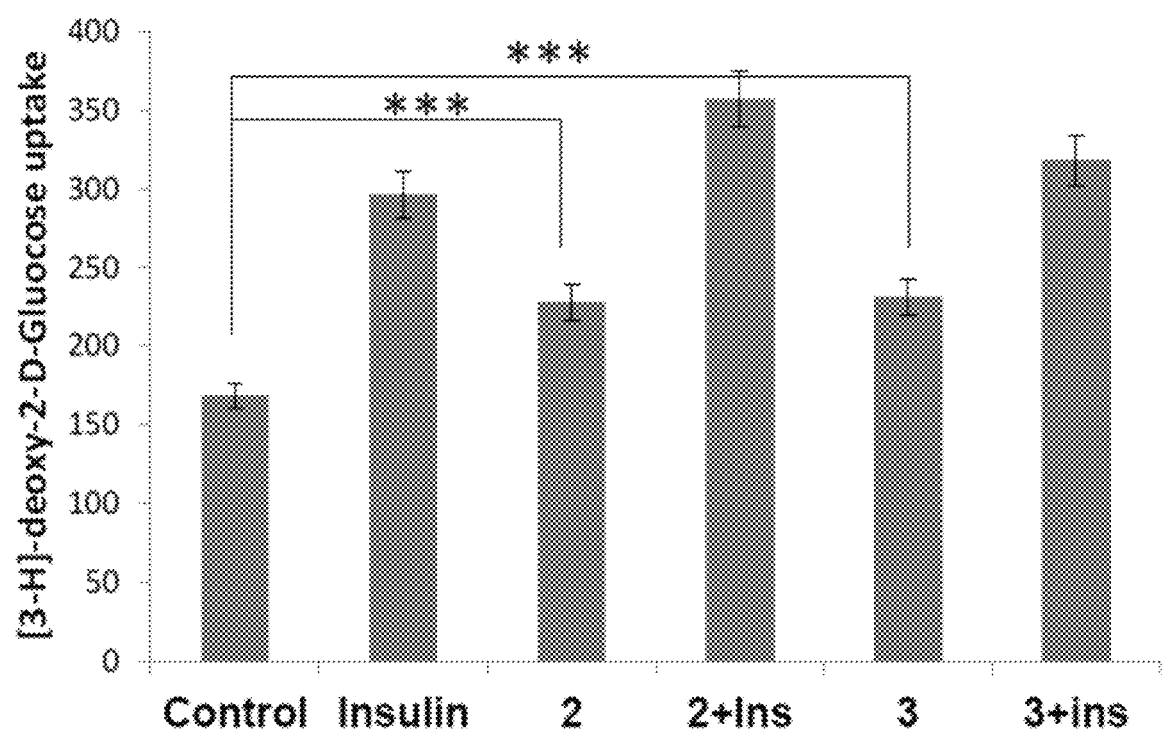
FIG. 12 shows a bar graph of glucose uptake when 2-(3,5-dioxo-4-azatricyclo[5.2.1.0(2,6)]dec-8-en-4-yl)-4-methylpentanoic acid (2) or 4-[(3,4-dichlorophenyl)amino]-3-(3-methylbenzyl)-4-oxobutanoic acid (3), according to embodiments of the invention were added to 3T3L1 cells for 24 h measured four times, where $p<0.001$ and highly significant by a two-tailed Student's t-test.

To examine glucose uptake, 3T3L1 cells were treated on day 3 of differentiation with either 2-(3,5-dioxo-4-azatricyclo[5.2.1.0(2,6)]dec-8-en-4-yl)-4-methylpentanoic acid or 4-[(3,4-dichlorophenyl)amino]-3-(3-methylbenzyl)-4-oxobutanoic acid at 500 nM concentration and maintained in culture up to day 8 when the cells mature into adipocytes with well-developed lipid bodies. After 100 nM insulin was added to cells and maintained for 30 minutes, [3-H]-deoxy-2-D-Glucose uptake was measured. As indicated in FIG. 12, an increase in glucose uptake was observed in the presence or either compound, and the uptake was further increased by addition of insulin. These results indicate that the small molecule compounds according to embodiments of the invention function to stabilize sortilin and promote glucose uptake.

It should be understood that the examples and embodiments described herein are for illustrative purposes only and that various modifications or changes in light thereof will be suggested to persons skilled in the art and are to be included within the spirit and purview of this application.

We claim:

1. A method of treating a diabetic patient, comprising:
   administering a pharmaceutical composition to a diabetic patient in an amount effective to stabilize sortilin and increase blood glucose uptake in said patient;
   wherein the pharmaceutical composition comprises a vehicle for administration to a patient, and a 2-substituted 3-oxo-1,2,3,4-tetrahydro-2-quinoxaline compound of formula (I),

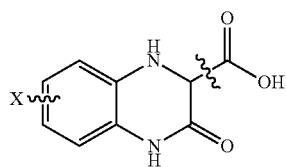

where x is H, C1-C5 alkyl, acyl, amino, chloro, bromo, iodo, or fluoro and where the carboxylic acid may be separated from the ring by one to three carbons which may be substituted with a C1 to C5 alkyl.

2. The method of claim 1, wherein administration occurs intravenously, orally, rectally, sublingually, sublabially, epidurally, intracerebrally, intracerebroventrically, topically, nasally, intervitrally, subcutaneously, transdermally, or by inhalation.

3. The method of claim 1, wherein the 2-substituted 3-oxo-1,2,3,4-tetrahydro-2-quinoxaline is (3-oxo-1,2,3,4-tetrahydro-2-quinoxalinyl)acetic acid.

4. The method of claim 1, wherein the vehicle for administration comprises one or more solvents, buffering agents, transporters, salts, binders, fillers, disintegrants, lubricants, encapsulates, emulsifiers, suspending agents, penetration enhancers, flavoring agents, preservatives, propellants, and/or coloring agents.

* * * * *